United States Patent [19]

Brahn

[11] Patent Number: 5,583,153
[45] Date of Patent: Dec. 10, 1996

[54] USE OF TAXOL IN THE TREATMENT OF RHEUMATOID ARTHRITIS

[75] Inventor: Ernest Brahn, Encino, Calif.

[73] Assignee: Regents of the University of California, Oakland, Calif.

[21] Appl. No.: 319,236

[22] Filed: Oct. 6, 1994

[51] Int. Cl.$^6$ ............................................. A61K 31/335
[52] U.S. Cl. ............................................. 514/449; 514/475
[58] Field of Search ...................................... 514/449, 475

[56] References Cited

PUBLICATIONS

Brahn et al; "Regression of Collagen–Induced Arthritis with Taxol, a Microlubule Stabilizer", Arthritis and Rheumatism; vol. 37, 14.0.6, Jun. 1994, pp. 839–845.

S. J. Oliver et al., "Suppression of Collagen–Induced Arthritis Using an Angiogenesis Inhibitor, AGM–1470, and a Microtubule Stabilizer, Taxol," Cell. Immunol. 157:291–299 (1994).

E. K. Rowinsky, "Taxol: A Novel Investigational Antimicrotubule Agent," J. Nat. Cancer Inst. 82: 1247–1259 (1990).

C. M. Spencer & D. Faulds, "Paclitaxel: A Review of Its Pharmacodynamic and Pharmacokinetic Properties and Therapeutic Potential in the Treatment of Cancer," Drugs 48:794–847 (1994).

D. Bissett & S. B. Kaye, "Taxol and Taxotere—Current Status and Future Prospects," Eur. J. Cancer 29A: 1228–1231 (1993).

J. G. Kuhn, "Pharmacology and Pharmacokinetics of Paclitaxel," Ann. Pharmacother. 28: S15–S18 (1994).

D. S. Sonnichsen & M. V. Relling, "Clinical Pharmacokinetics of Paclitaxel," Clin. Pharmacokinet. 27: 256–269 (1994).

D. R. Kohler & B. R. Goldspeil, "Evaluation of New Drugs: Paclitaxel (Taxol)," Pharmacotherapy 14: 3–34 (1994).

J. L. Eiseman et al., "Plasma Pharmacokinetics and Tissue Distribution of Paclitaxel in $CD_2F_1$ Mice," Cancer Chemother. Pharmacol. 34: 465–471 (1994).

E. D. Harris, Jr., "Rheumatoid Arthritis: Pathophysiology and Implications for Therapy," New Eng. J. Med. 322: 1277–1289 (1990).

D. Ingber et al., "Synthetic Analogues of Fumagillin that Inhibit Angiogenesis and Suppress Tumor Growth," Nature 348: 555–557 (1990).

(Abstract) C. Tang et al., "Regression of Collagen–Induced Arthritis with Taxol, a Microtubule Stabilizer," Arth. Rheum. 36 (Supplement): S45 (1993).

Primary Examiner—Theodore J. Criares
Attorney, Agent, or Firm—Merchant, Gould, Smith, Edell, Welter & Schmidt

[57] ABSTRACT

An improved method of suppression of a progressive, inflammatory, autoimmune arthritis in a mammal involves the use of the drug Taxol. In general, such a method comprises administering to a mammal having or susceptible to arthritis Taxol in a pharmacologically acceptable carrier capable of solubilizing Taxol in a dose sufficient to suppress at least one symptom of arthritis selected from the group of inflammation, swelling, abnormal neovascularization, bone erosion, and cartilage erosion. The use of Taxol can be combined with the use of other antiarthritic drugs, such as the angiogenesis inhibitor AGM-1470, to produce a greater therapeutic effect than with either Taxol or the other antiarthritic drug alone.

15 Claims, 6 Drawing Sheets

FIG. 3A
FIG. 3B
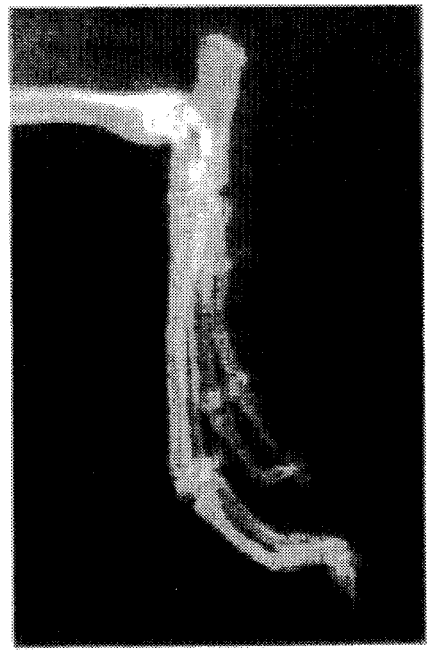
FIG. 3C
FIG. 3D

USE OF TAXOL IN THE TREATMENT OF RHEUMATOID ARTHRITIS

GOVERNMENT RIGHTS

This invention was supported by grants from the United States government, namely Grant Nos. AR-38884, AR-36834, AR-40919, and AR-42200, from the National Institutes of Health. Accordingly, the government may have certain rights in this invention.

BACKGROUND OF THE INVENTION

This invention is directed to a method of suppression of a progressive, inflammatory, autoimmune arthritis in a mammal, such as rheumatoid arthritis. Despite advances in treatment, arthritis remains an extremely serious health problem, particularly in view of the aging population in the United States and other developed countries, because arthritis is typically a disease of the elderly. Although rarely fatal, arthritis is a major cause of morbidity, loss of time from work, lost productivity and decrease in quality of life. It causes severe pair and loss of joint mobility and can make doing even simple tasks difficult.

Among the most serious forms of arthritis is rheumatoid arthritis. Rheumatoid arthritis is generally believed to be an autoimmune disease that is believed to be associated with activity of autoreactive T cells. It is believed that these cells cause the disease via a delayed-type hypersensitivity reaction. Although it is not completely certain which antigen these T cells recognize, one significant candidate is type II collagen. The possibility exists that other antigens may also play a role in the disease.

Substantial work has been done on genetic bases for susceptibility to the disease. This work has focused on MHC haplotypes. Thus, it may be possible to determine, from familial studies or direct genomic analysis, that some individuals are at particular risk for the development of rheumatoid arthritis.

Although a number of treatment methods and regimes exist for rheumatoid arthritis, none of them is as yet completely satisfactory. These treatment regimens include administration of non-steroidal anti-inflammatory drugs such as acetylsalicylic acid (aspirin), ibuprofen, naproxen, and other such agents, gold compounds, penicillamine, 4-aminoquinoline agents, and immunomodulators.

Collagen-induced arthritis (CIA) is a T-cell dependent animal model of rheumatoid arthritis (RA) (D. E. Trentham et al., "Autoimmunity to Type II Collagen: An Experimental Model of Arthritis," *J. Exp. Med.* 146: 857–868 (1977)). Within two weeks after immunization with type II collagen (CII) in IFA, susceptible rats develop polyarthritis with histologic changes of pannus formation and bone/cartilage erosion. In addition, humoral and cellular responses to CII occur in CIA as well as RA (E. Brahn, "Animal Models of Rheumatoid Arthritis: Clues to Etiology and Treatment" in *Clinical Orthopedics and Related Research* (B. Hahn, ed., Philadelphia, JB Lippincott Company, 1991). Consequently, CIA is a useful animal model of RA that serves as an in vivo system for the exploration of inflammatory synovitis etiologies and for the investigation of potentially new therapeutic interventions.

However, there exists a need for an improved treatment of rheumatoid arthritis and other autoimmune forms of arthritis that can suppress or ameliorate symptoms such as inflammation, swelling, abnormal neovascularization, bone erosion, or cartilage erosion. Preferably, such an improved method of treatment should be able to be combined with other treatment methods, should work rapidly to cause regression or stabilization of symptoms, and should be well tolerated. Preferably, such a treatment regimen should also be adaptable to prophylaxis in susceptible individuals.

SUMMARY

An improved method of suppression of a progressive, inflammatory, autoimmune arthritis in a mammal involves the use of the drug Taxol. Taxol is undergoing wide evaluation for treatment of malignancies, but has not been evaluated or proposed for the treatment of arthritis.

In general, a method according to the present invention comprises administering to a mammal having or susceptible to arthritis Taxol in a pharmacologically acceptable carrier capable of solubilizing Taxol in a dose sufficient to suppress at least one symptom of arthritis selected from the group of inflammation, swelling, abnormal neovascularization, bone erosion, and cartilage erosion.

The mammal can be a rat, in which case the arthritis can be collagen-induced arthritis.

Alternatively, the mammal can be a human being, in which case the arthritis can be rheumatoid arthritis.

Typically, the pharmacologically acceptable carrier is a 1:1 dilution of ethanol and cremophor EL, further diluted with saline.

Typically, the dose sufficient to suppress at least one symptom of arthritis is from about 7.5 mg/kg body weight to about 10 mg/kg body weight of Taxol. However, lower doses can be used, such as from about 0.075 mg/kg body weight to about 0.1 mg/kg body weight, or from about 0.75 mg/kg body weight to about 1 mg/kg body weight.

Alternatively, derivatives of Taxol substituted on the diterpene nucleus can be used in place of Taxol.

Another aspect of the present invention is the use of Taxol in combination with another antiarthritic drug. The antiarthritic drug other than Taxol can be selected from the group consisting of a nonsteroidal antiinflammatory agent, an organic gold derivative, D-penicillamine, a 4-aminoquinoline, azathioprine, methotrexate, cyclosporin, an angiogenesis inhibitor, a monoclonal antibody to T cells, a monoclonal antibody to an adhesion molecule, and a monoclonal antibody to a cytokine or growth factor.

A preferred antiarthritic drug other than Taxol for combination therapy is the angiogenesis inhibitor AGM-1470.

A preferred method for combination therapy comprises:
(1) administering to a mammal having or susceptible to arthritis Taxol in a pharmacologically acceptable carrier capable of solubilizing Taxol in a dose sufficient to suppress at least one symptom of arthritis selected from the group of inflammation, swelling, abnormal neovascularization, bone erosion, and cartilage erosion; and
(2) administering to the mammal the angiogenesis inhibitor AGM-1470 in a dose sufficient to suppress at least one symptom of arthritis.

The administration of both Taxol and AGM-1470 produces a greater degree of suppression of at least one symptom of arthritis than does the administration of the equivalent dose of either Taxol or O-(chloroacetylcarbamoyl) fumagillol (AGM-1470) alone

BRIEF DESCRIPTION OF THE DRAWINGS

These and other features, aspects, and advantages of the present invention will become better understood with reference to the following description, appended claims, and accompanying drawings where:

FIG. 3A is a photograph of a limb from a control group rat 28 days after immunization with type II collagen (Example 1), showing swelling and other changes characteristic of arthritis;

FIG. 3B is a radiograph of the limb shown in FIG. 3A, showing soft tissue inflammation and bone destruction;

FIG. 3C is a photograph of a limb from a rat 28 days after immunization with type II collagen treated with high-dose Taxol, showing no swelling or other changes characteristic of arthritis;

FIG. 3D is a radiograph of the limb shown in FIG. 3C, showing the absence of soft tissue inflammation and bone destruction, contrasted with FIG. 3B;

DESCRIPTION

I have developed a method for suppression of a progressive, inflammatory, auto-immune arthritis in a mammal using the antineoplastic drug Taxol. As used herein, the term "suppression" includes any or all of the following: (1) amelioration of existing symptoms; (2) prevention of pro-gression of symptomatology in these progressive disease processes; (3) prevention of the inception or occurrence of the disease in a susceptible subject, i.e., prophylaxis.

Figure 1:
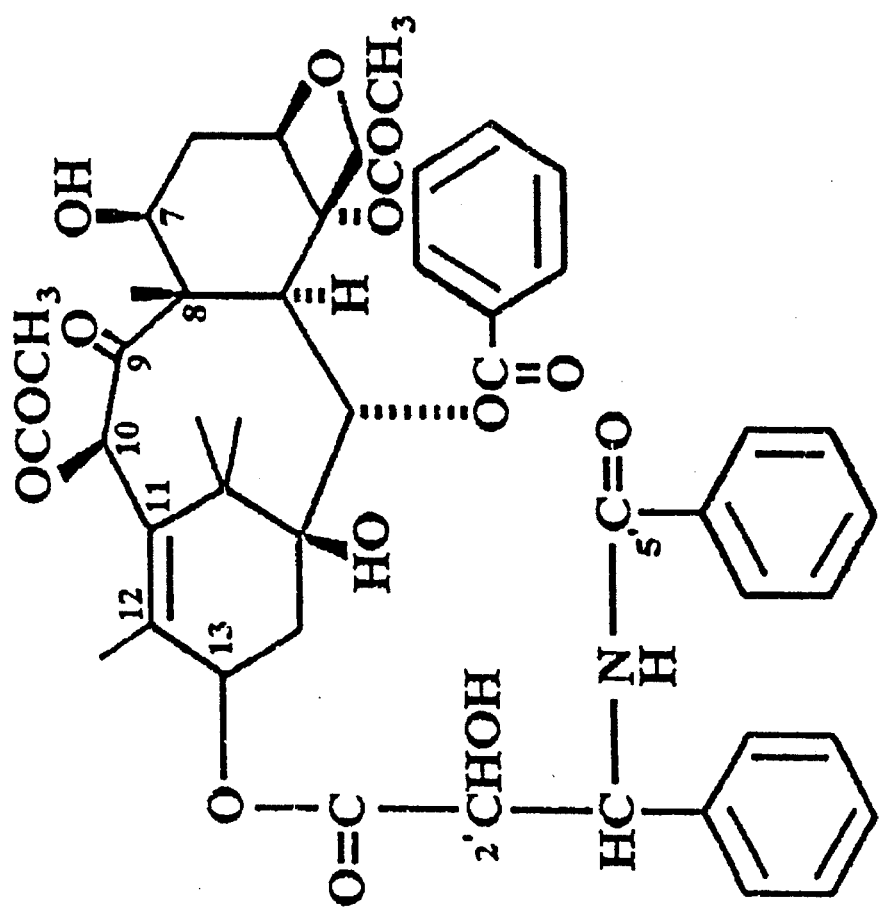
FIG. 1 is the structural formula of Taxol.

The method of treatment of the present invention uses Taxol, a microtubule stabilizer. Taxol, whose structure is shown in FIG. 1, is an extremely hydrophobic diterpene extracted from the dried inner stem bark of the Western yew, *Taxus brevifolia* (M. C. Wani et al., "Plant Antitumor Agents VI. The Isolation of Structure of Taxol, A Novel Antileukemic and Antitumor Agent from Taxus Brevifolia," *J. Am. Chem. Soc.* 93: 2325–2327 (1971)) which grows primarily in old-growth forests of the Pacific Northwest. The compound has a complex ring structure, with an ester side chain at position C-13 that confers bioactivity in mammalian systems (S. B. Horwitz, "Mechanism of Action of Taxol," *Trans Pharmacol. Sci.* 13: 134–136 (1992)) It has antineoplastic activity against a number of neoplastic cell strains frequently used as models for Cancer (P. H. Wiernik et al., "Phase One Clinical and Pharmacokinetic Study of Taxol," *Cancer Res.* 47: 2486–2493 (1987)). Attempts to synthesize the compound are critical, since at present, the isolation of enough Taxol for one patient-year of treatment requires more than sixty pounds of tree bark. Taxol has now been partially synthesized from the needles of the European Yew tree and more recently by a totally synthetic pathway (K. C. Nicolaou et al., "Total Synthesis of Taxol," *Nature* 367: 630–634 (1994)).

Studies have demonstrated that Taxol has a unique mechanism of action. Unlike other antimicrotubule agents that depolymerize microtubules, e.g., colchicine and vinblastine, Taxol has been shown to enhance microtubule polymerization by preferentially binding to the β subunit of tubulin and shifting the dynamic equilibrium from tubulin dimers to stable microtubule polymers, even in the absence of GTP and microtubule associated proteins that are normally required (S. B. Horwitz (1992), supra; P. B. Schiff & S. B. Horwitz, "Promotion of Microtubule Assembly in Vitro by Taxol," *Nature* 277: 665–667 (1979)); N. Kumar, "Taxol-Induced Polymerization of Purified Tubulin," *J. Biol. Chem.* 256: 10435–10441 (1981)). Because Taxol blocks reorganization of the microtubule cytoskeleton (E. B. Horwitz (1992), supra; P. B. Schiff & S. B. Horwitz, "Taxol Stabilizes Microtubules in Mouse Fibroblast Cells," *Proc. Natl. Acad. Sci. U.S.A.* 77: 1561–1565 (1980)), it inhibits cell division at the late $G_2$ mitotic phase. This effect on mitotic spindles has been suggested as the primary mechanism as an antitumor agent, although microtubules are also important in many other functions including cell migration, phagocytosis, chemotaxis, adhesion and intracellular transport (E. B. Horwitz (1992), supra; R. L. Roberts et al., "Effects of Taxol on Human Neutrophils," *J. Immunol.* 129: 2134–2141 (1982); A. Iannone et al., "Taxol Inhibits N-Formyl Methionyl-Leucyl-Phenylalanine (FMLP) Induced Neutrophil Polarization and $H_2O_2$ Production While Decreasing [$^3$H]FMLP Binding," *Agents Actions* 21: 278–280 (1987); S. L. Newman et al., "Differential Requirements for Cellular Cytoskeleton in Human Macrophage Complement Receptor-Fc Receptor-Mediated Phagocytosis," *J. Immunol.* 144: 967–974 (1991)). Recent studies also indicate that Taxol may also have additional antineoplastic activity by up-regulating tumor necrosis factor α (TNF α) and interleukin-1 (C. Bogdan & A. Ding, "Taxol, a Microtubule-Stabilizing Antineoplastic Agent, Induces Expression of Tumor Necrosis Factor a and Interleukin-1 in Macrophages," *J. Leukoc. Biol.* 52: 119–121 (1992); C. Bottex-Gauthier et al., "The Effects of Taxol on the Macrophage Function: Interaction with Some Immunological Parameters," *Immunopharmacol. Immunotoxicol,* 14: 39–61 (1992); C. L. Manthey et al., "Taxol Increases Steady-State Levels of Lipopolysaccharide-Inducible Genes and Protein Tyrosine Phosphorylation in Murine Macrophages," *J. Immunol.* 149: 2459–2465 (1992)).

Accordingly, a method of suppression of such autoimmune arthritis diseases comprises administering to a mammal having or susceptible to arthritis Taxol in a pharmacologically acceptable carrier capable of solubilizing Taxol in a dose sufficient to suppress at least one symptom of arthritis selected from the group of inflammation, swelling, abnormal neovascularization, bone erosion, and cartilage erosion.

The mammal can be a rat, in which case the arthritis can be collagen-induced arthritis, a well-recognized model for rheumatoid arthritis in humans (see example 1).

Alternatively, the mammal can be a human being and the arthritis can be rheumatoid arthritis.

The pharmacologically acceptable carrier is preferably a 1:1 dilution of ethanol and cremophor EL (Sigma Chemical Co. St. Louis, Mo.), further diluted with saline. Other pharmacologically acceptable carriers capable of solubilizing Taxol exist and are known in the art. Other agents, such as buffers, stabilizers, and preservatives, can optionally be added as needed.

In one alternative, the dose sufficient to suppress at least one symptom of arthritis is from about 7.5 mg/kg body weight to about 10 mg/kg body weight of Taxol. Typically, in this alternative, a dose of about 10 mg/kg body weight is used, referred to as full-dose Taxol. However, without being bound by this theory, Applicant believes that, in accord with the experience gained with the use of other antineoplastic drugs in rheumatoid arthritis, a dosage of one to two orders of magnitude less may be appropriate in suppressing arthritis without leading to side effects. This would lead to a dosage of as low as 0.1 mg/kg body weight. For example, dosages of about 0.75 mg/kg body weight to about 1.0 mg/kg body weight or of about 0.075 mg/kg body weight to about 0.1 mg/kg body weight can be used. Of course, intermediate dosages can also be used. Even lower dosages may be of benefit.

Typically, administration of Taxol occurs at 2–3 day intervals (see Example 1). However, again in accord with the experience gained with the use of other antineoplastic drugs in rheumatoid arthritis, administration may occur less frequently, e.g., weekly, biweekly, or even monthly.

Preferably, administration is intravenous or intraperitoneal. Other injection routes can also be used, and are known in the art. Alternatively, the drug can be administered orally.

The most effective mode of administration and dosage regimen for Taxol as used in the methods of the present invention depend on the severity and course of the disease, the patient's health, the response to treatment, pharmacokinetic considerations such as the condition of the patient's liver and/or kidneys that can affect the metabolism and/or excretion of the administered Taxol, and the judgment of the treating physician. Accordingly, the dosages should be titrated to the individual patient.

Another aspect of the present invention is a method of combination therapy in which an antiarthritic drug other than Taxol is administered to the mammal along with Taxol. This other antiarthritic drug can be any of the following: (1) a nonsteroidal anti-inflammatory agent such as acetylsalicylic acid (aspirin), ibuprofen, or naproxen; (2) an organic gold derivative such as gold sodium thiomalate, aurothioglucose, or auranofin; (3) D-penicillamine; (4) a 4-aminoquinoline agent such as hydroxychloroquine; (5) azathioprine; (6) methotrexate; (7) cyclosporin; (8) an angiogenesis inhibitor such as AGM-1470; (9) monoclonal antibodies to T cells; (10) monoclonal antibodies to adhesion molecules and (11) monoclonal antibodies to cytokines and growth factors.

A particularly preferred antiarthritic drug other than Taxol for combination therapy is the angiogenesis inhibitor AGM-1470, as described below in Example 2.

The dosage for the antiarthritic drug other than Taxol can be determined by the treating physician in much the same way as the Taxol dose. A typical high dose regimen for the preferred angiogenesis inhibitor AGM-1470 is 27.5 mg/kg, administered every other day, but, as with Taxol, this agent can be administered at lower dosages and at a lower frequency.

When Taxol is administered in combination with another antiarthritic drug, the administration of both Taxol and the other antiarthritic drug produces a greater degree of suppression of at least one symptom of arthritis than does the administration of the equivalent dose of either Taxol or the other antiarthritic drug alone. This has been demonstrated for AGM-1470 (Example 2).

Alternatively, in place of Taxol, derivatives of Taxol can be used in a method according to the present invention. Such derivatives can be substituted on the diterpene nucleus, leaving the ester substituent at C-13 which is significant for bioactivity, as discussed above. The substituents can include lower alkyl ($C_1$–$C_5$), halogen, hydroxyl, and other groups. The side chains such as the ester groups and the benzoyloxy group can also be substituted, such as on the methyl moieties of the ester linkage or the aromatic moiety of the benzoyloxy group. Such substituents may improve solubility or stability.

The present invention is illustrated by the following Examples. The Example are for illustrative purposes only and are not intended to limit the invention.

EXAMPLES

Regression of Collagen-Induced Arthritis in Rats by Treatment With Taxol

Materials and Methods

Animals

Syngeneic female Louvain (LOU) rats (120–150 g), housed in the UCLA vivarium, were used in all experimental protocols.

Arthritis Induction

Rats, under ether anesthesia, were injected intradermally with 0.5 mg of native chick collagen type II (CII) (Genzyme, Boston, Mass.) solubilized in 0.1M acetic acid and emulsified in IFA (Difco, Detroit, Mich.) (D. E. Trentham et al., "Autoimunity to Type II Collagen: An Experimental Model of Arthritis," *J. Exp. Med.* 146: 857–868 (1977)). Between 90–100% of rats typically develop synovitis by day 9 post-immunization.

Experimental Design

Taxol (Sigma, St. Louis, Mo.) was initially solubilized in a 1:1 dilution of ethanol and cremophor EL (Sigma, St. Louis, Mo.). Normal saline was added to make a final concentration of 4.8 mg/ml Taxol in 5% w/v ethanol and 5% w/v cremophor EL prior to administration by i.p. injection. A total of 45 rats in four protocols were used: a control group that received vehicle alone, and three Taxol treatment groups consisting of a prevention and two suppression protocols. In the prevention protocol, 1 mg/kg body weight of Taxol was administered on day 2 after CII immunization in an attempt to preclude CIA induction. Five subsequent doses were given on days 5, 7, 9, 12, and 14. In the two suppression protocols, rats were allowed to develop arthritis and Taxol was then given on alternate days beginning on the day of arthritis onset (day 9). In the "high dose" suppression protocol, full dose (1 mg/kg body weight) Taxol was used until day 19 when it was discontinued. In the "low dose" suppression protocol, because of concerns about potential toxicity with the higher dosage schedule, Taxol (10 mg/kg body weight) was administered on days 9, 11, 13 and then 75% of this dose (7.5 mg/kg body weight) was continued on alternate days through day 21. The dose administered on day 21 was added in an attempt to extend the benefits of Taxol since preliminary data indicated that recrudescence of arthritis could occur after discontinuation of Taxol. Final body weights were determined on day 28 at the completion of the study.

Arthritis Assessment

The incidence and severity of the arthritis were both evaluated. The incidence was determined by the number of rats with clinical evidence of joint inflammation during the study period. The severity of inflammation of each paw was evaluated daily by the same investigator using an integer scale that ranged from 0 to 4. This quantification method scale was based on increasing standardized levels of swelling and periarticular erythema with 0 being normal and 4 being severe. Scores were independently confirmed by other investigators throughout the study with excellent inter-observer agreement. The sum of the scores for all four limbs (maximum score=16) is the arthritic index for each rat (D. E. Trentham (1977), supra; R. T. Schoen et al., "Antigen-Specific Suppression of Type II Collagen-Induced Arthritis by Collagen-Coupled Spleen Cells," *J. Immunol.* 128: 717–719 (1982); D. E. Trentham & C. E. Brinckerhoff, "Augmentation of Collagen Arthritis by Synthetic Analogues of Retinoic Acid," *J. Immunol.* 129: 2668–2672 (1982)). An index score between 6 and 8 is considered severe disease since CIA usually affects only hind limbs. Photographs of selected limbs were obtained on day 28.

Radiographic scores, determined by an investigator blinded to treatment intervention, were determined for the hind limbs on day 28 by the extent of soft tissue swelling, joint space narrowing, bone destruction, and periosteal new bone formation (E. Brahn & D. E. Trentham, "Antigen Specific Suppression of Collagen Arthritis by Adoptive Transfer of Spleen Cells," *Clin. Immunol. Immunopathol.* 31: 124 (1984)). An integer scale from 0 to 3 was used to quantify each limb (0=normal, 1=soft tissue swelling, 2=early erosions of bone, 3=severe bone destruction and/or ankylosis). The scores were assigned by a blinded investigator. The sum of both hind limb scores for each rat represented the radiographic joint index (maximum score per rat=6) (D. E. Trentham & C. E. Brinckerhoff (1982), supra; E. Brahn & D. E. Trentham (1984), supra).

Histologic Analysis

Hind limbs were randomly selected on day 28 from the control and Taxol treated groups for histologic analysis by a pathologist blinded to treatment protocols. Thymuses and spleens were also harvested for weight determination and histologic evaluation. Hematoxylin and eosin stained sections were reviewed by a blinded pathologist using light microscopy.

Immune Responses

Delayed type hypersensitivity (DTH) to CII was determined by a radiometric ear assay completed on day 28 (D. E. Trentham & C. E. Brinckerhoff (1982), supra; W. J. McCune et al., "Gold Does Not Alter the Arthritic, Humoral, or Cellular Responses in Rats with Type II Collagen-Induced Arthritis," *Arthritis Rheum.* 23: 932–936 (1980)). Based on previous studies, radiometric ear indices $\geq 1.4$ represent a significant response to CII. The presence of anti-CII IgG antibodies was determined by an enzyme-linked immunosorbent assay (ELISA) (D. E. Trentham & R. A. Dynesius-Trentham, "Attenuation of an Adjuvant Arthritis by Type II Collagen," *J. Immunol.* 130: 2689–2692 (1983); G. Ku et al., "Prevention of Experimental Autoimmune Arthritis with a Peptide Fragment of Type II Collagen," *Eur. J. Immunol.* 23: 591–599 (1993); D. Peacock et al., "Angiogenesis Inhibition Suppresses Collagen Arthritis," *J. Exp. Med.* 175: 1135–1138 (1992)). Serum samples were obtained on day 26, diluted to 1: 2560, and the results were expressed as the mean optical density at 490 nm of quadruplicate aliquots. The 1: 2560 dilution was chosen because it represents the mid-linear portion of a standardized ELISA curve for pooled arthritic rat serum that was evaluated concurrently with the experimental serum. Normal rat serum backgrounds at this dilution are zero and readily distinguishable from collagen-immunized rat serum.

Statistics

Students' t-test was used to evaluate the group means of the continuous variables. The Chi square test was used to evaluate the proportionate group frequencies of dichotomous variables. Yeats' correction was used where indicated and the results were defined as significant at the $P<0.05$ level.

Results

Clinical Evaluations

Figure 2:
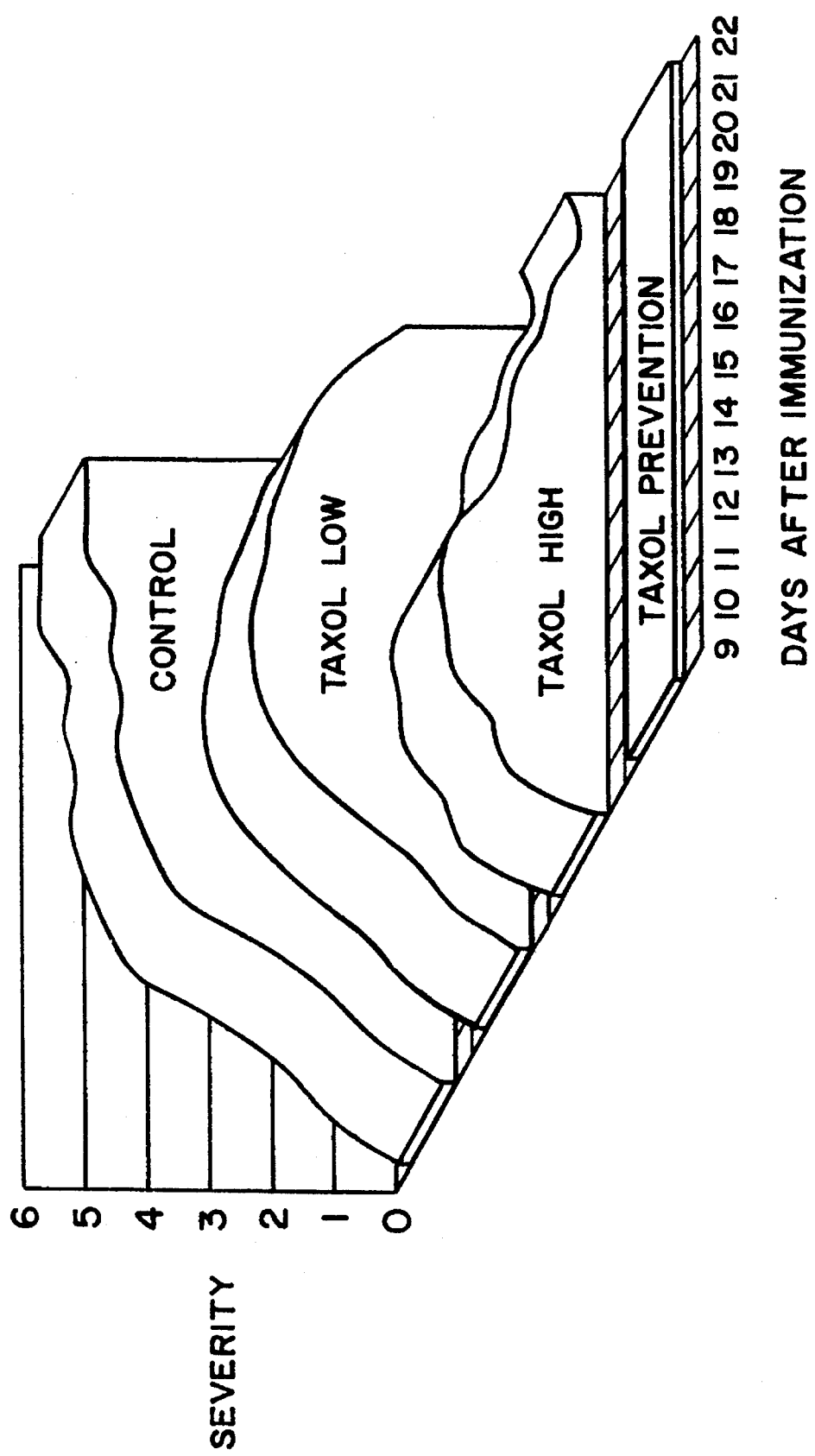
FIG. 2 is a graph showing arthritis severity in rats as a function of the number of days after immunization with type II collagen for rats left untreated, rats treated with low-dose Taxol, and rats treated with high-dose Taxol.

None of the rats in the Taxol prevention protocol developed arthritis (even after discontinuation of Taxol) compared to 94% in the vehicle control group (Table 1). Since all rats were required to have arthritis prior to entry into either of the two Taxol suppression protocols, the incidence of arthritis was 100% in these groups. Within 5 days of Taxol institution, both high and low dose protocols demonstrated clear reductions in arthritis severity compared to controls (FIGS. 2 and 3). The study protocol required that all rats in the low-dose and high-dose Taxol arthritis suppression protocols (Taxol Low and Taxol High in FIG. 2) have arthritis prior to the institution of taxol. None of the rats in the taxol arthritis prevention protocol developed arthritis. Arthritis severity nadirs occurred by day 21 ($P<0.0000001$ and $P<0.0001$ for the high and low dose groups, respectively). These rats were observed for an additional week after discontinuation of Taxol and, within the first 3 or 4 days of this wash out period, a return of soft tissue swelling was evident in some rats.

TABLE 1

Clinical and Radiographic Effects of Taxol on Collagen-Induced Arthritis

| | Control rats | Taxol-treated rats, prevention protocol | Taxol-treated rats. suppression protocol | |
|---|---|---|---|---|
| | | | High-dose | Low-dose |
| No. of rats | 17 | 8 | 10 | 10 |
| Clinical incidence of arthritis, % | 94 | 0* | 100† | 100† |
| Clinical severity of arthritis (day 21), mean ± SEM | 5.9 ± 0.5 | 0‡ | 0.7 ± 0.3‡ | 2.0 ± 0.5* |
| Radiographic score (day 28), mean ± SEM | 4.0 ± 0.4 | 0§ | 1.2 ± 0.2* | 1.3 ± 0.2¶ |
| Radiographic erosions (day 28), % | 94# | 0* | 0** | 20¶ |

*P < 0.0001 compared with controls.
†The taxol suppression protocols required that the rats have arthritis prior to therapeutic intervention.
‡P < 0.0000001 compared with controls.
§P < 0.000001 compared with controls.
¶P < 0.001 compared with controls.
All 16 rats in this group that had clinical arthritis also had erosions.
**P < 0.00001 compared with controls.

Rats that tolerated their Taxol therapy had stable weights throughout the study that were comparable to higher, but not significantly different, than the control group. No deaths were noted in the prevention protocol, possibly because they received the fewest Taxol doses and at no point developed the intercurrent illness of CIA. Three rats in the more protracted low dose regimen and one rat in the high dose protocol developed late onset weight loss, diarrhea, and subsequently died (median death at 25 days post CII immunization). Both of these sequelae have been described in humans administered Taxol for advanced cancer therapy. All other rats, aside from the development of arthritis, appeared healthy. Peripheral blood hematocrits and white blood cell counts were similar in all groups although rats intolerant of Taxol had a selective neutropenia (another recognized consequence observed in human studies) that may predispose them to infectious complications.

Radiographic Scores

Hind limb radiographs were obtained and blindly read on day 28. None of the rats in the Taxol prevention protocol (which also lacked any clinical arthritis) manifested any radiographic changes compared to 94% in the control group (Table 1). Since rats in either of the Taxol suppression protocol groups had been off therapy for at least a week by day 28, their radiographic index primarily reflects the recrudescence of soft tissue swelling during this interval. Both the high and low dose Taxol groups had significantly less disease (FIG. 3C and 3D, Table 1) compared to controls. Only 2 of the 28 total Taxol recipients (7%) demonstrated any evidence of even minimal erosions (all in the low dose suppression group) compared to 94% with erosions in the control group. All of the 16 control rats with clinical arthritis had significant erosions (100%) and the single rat without clinical arthritis also lacked radiographic changes.

Synovial Pathology

Figure 4B:
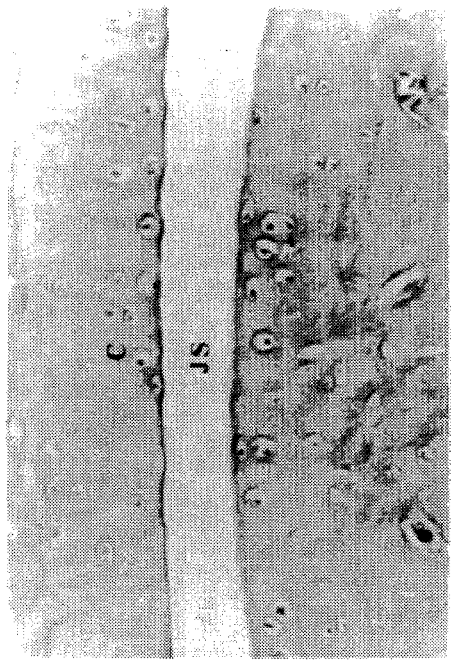
FIG. 4B is a photomicrograph of a synovial section from a rat treated with high-dose Taxol, demonstrating minimal if any pannus, with preservation of articular cartilage (C=cartilage; JS=joint space)
Figure 4A:
FIG. 4A is a photomicrograph of a synovial section from an arthritic control group rat, demonstrating marked pannus, with bone and cartilage erosion (P=pannus; C=cartilage; JS=joint space)

Synovial sections obtained from control group rats demonstrated marked pannus with bone and cartilage erosions (FIG. 4A; P=pannus, C=cartilage, J=joint space). In general, Taxol treated rats had minimal if any pannus with preservation of articular cartilage (FIG. 4B; C=cartilage, J=joint space).

Immunologic Effects

The mean delayed-type hypersensitivity (DTH) responses in the Taxol treated groups were not significantly different from the control group (Table 2). The mean IgG anti-CII antibody titer as measured by ELISA, however, was significantly higher in the control group compared to the prevention and suppression groups (Table 2). Blinded histologic evaluation of thymuses and spleens showed no overt histologic changes compared to controls. Spleen weights, however, were higher in the Taxol treated rats (392 mg±18 vs 299±44, P<0.05). Taxol recipients tended to weigh more than the severely arthritic controls. If the spleen sizes were compared as a percentage of body weight, there were no significant differences.

This is the first study to evaluate Taxol in an autoimmune disease. The experiments demonstrate that Taxol could completely abrogate arthritis onset if initiated 2 days after CII immunization. There was a marked reduction in CIA severity after 3 injections of Taxol for established arthritis and the "high dose" protocol was more effective than the "low dose" protocol. The severity of arthritis continued to decrease throughout the duration of Taxol administration but began to rise within four days after the cessation of treatment in both suppression protocols. This suggests that chronic intermittent therapy is needed to control established CIA, possibly because in the absence of Taxol, which has a rapid systemic clearance, microtubule stabilization is not static and is in constant equilibrium with the $\alpha$ and $\beta$ tubulin dimers. In contrast, early intervention with Taxol (prevention protocol) appeared to attenuate the need for continuous therapy. This might be due to Taxol's inhibition of CII phagocytosis and/or processing to a recently identified pathogenic 12 mer epitope (G. Ku et al. (1993), supra), both microtubule dependent steps. The impact of Taxol on CIA is relatively rapid since permanent joint damage, as defined by radiographically evident erosions, was precluded.

Because microtubule function is important in multiple physiologic processes, further studies are needed to clarify the critical immunologic and inflammatory effects of Taxol therapy on autoimmune mechanisms. Although overall DTH responses to whole CII were not significantly altered, prior studies in CIA indicate that afferent sensitization to 99% of the parent molecule, excluding the pathogenic epitope at position 62–73 on cyanogen bromide fragment 11, are not predictive of disease susceptibility in Louvain rats (G. Ku et al. (1993), supra). Only a limited repertoire of $CD4^+T$ cell clones, that recognize this processed sequence, are necessary for CIA induction (D. Peacock et al. (1992), supra). Although antibodies to CII were statistically lower in Taxol recipients, the biological significance of this finding is unclear since all rats produced high titer anti-CII IgG antibodies. In addition to its inhibition of cell mitosis, migration, chemotaxis, and adhesion, Taxol can also suppress intracellular transport and neutrophil $H_2O_2$ production (E. Rowinsky et al., "Taxol: A Novel Investigational Antimicrotubule Agent,." *J. Nat. Cancer Inst.* 82: 1247–1257 (1990)). All these important components of the inflammatory response are linked to microtubule function. Taxol has recently been shown (C. Bottex-Gauthier et al. (1992), supra; C. L. Manthey et al. (1992), supra) to have complex effects on murine macrophage expression of TNF-$\alpha$ and TNF-$\alpha$-receptors by rapid induction of tyrosine phosphorylation of a 41- and 42 -kDa protein, a mechanism previously demonstrated with LPS. In macrophages exposed to Taxol, cell cycle-independent TNF-$\alpha$ transcription was upregulated but TNF-$\alpha$ receptors were actively internalized. This might

TABLE 2

| Immunologic Effects of Taxol on Collagen-Induced Arthritis | | | |
|---|---|---|---|
| | | Taxol-treated rats, prevention | Taxol-treated rats, suppression protocol |
| | Control rats | protocol | High-dose | Low-dose |
| IgG anti-collagen antibodies† | 0.17 ± 0.002 | 0.09 ± 0.007‡ | 0.13 ± 0.007‡ | 0.16 ± 0.002‡ |
| Delayed-type hypersensitivity | 3.06 ± 0.19 | 2.98 ± 0.25 | 3.09 ± 0.29 | ND |

*Assays were performed at day 28. Values are the mean ± SEM. ND = not done.
†Optical density at 490 nm, 1:2,560 dilution.
‡P < 0.01 compared with controls.

be an important mechanism given the critical role TNF-α plays in CIA (E. Brahn et al., "Effects of Tumor Necrosis Factor Alpha (TNF-α) on Collagen Arthritis," *Lymphokine Cytokine Res.* 11: 253–256 (1992))., In addition to its potential as a therapeutic agent, Taxol represents an important tool to study microtubule-dependent cellular events. It binds specifically to cells with a high affinity that is reversed with colchicine or vinblastine, agents that depolymerize microtubules (S. B. Horwitz (1992), supra). Taxol has already been used to isolate tubulin and microtubule-associated proteins from a variety of cells (S. B. Horwitz (1992), supra). Mutant tumors have also been developed that are either Taxol-resistant (because of aberrant tubulin subunits) or Taxol-dependent (for cell replication).

Taxol is a prototypic compound for a new class of potential antirheumatic agents. The study reported in this Example demonstrates that Taxol is a disease modifying drug in rat CIA. It could also be considered a candidate, because of its unique mechanism of action, for combination therapies (see Example 2). Further investigations of Taxol in CIA and other autoimmune diseases appear to be warranted.

EXAMPLE 2

Regression of Collagen-Induced Arthritis in Rats by Treatment With Taxol and an Angiogenesis Inhibitor As a refinement of the studies reported in Example 1, regression of collagen-induced arthritis in rats by treatment with Taxol and an angiogenesis inhibitor was studied.

Collagen induced arthritis (CIA) in rats is a T-cell dependent animal model of chronic inflammatory arthritis resulting in pannus and joint destruction similar to rheumatoid arthritis (RA) (D. E. Trentham (1977), supra). CIA is induced by intradermal injection of native collagen type II (CII) emulsified in incomplete Freund's adjuvant with reliable development of polyarthritis in greater than 90% of recipients 10 to 12 days later. Within 4 weeks of CIA induction, fulminant synovitis results in extensive erosions and frank ankylosis of involved joints. In addition, rats immunized with CII develop antibodies and delayed-type hypersensitivity (DTH) to the antigen (E. Brahn (1991), supra).

In adults, physiologic angiogenesis is usually limited to wound healing and reproductive functions. Abnormal neovascularization, however, contributes to pathologic states, including tumor growth, proliferative retinopathy, and inflammatory synovitis (J. Folkman & M. Klagsbrun, *Science,* 235: 442 (1987); E. S. Kimball & J. L. Gross, *Agents Actions,* 34: 329 (1991); D. J. Peacock et al., *J. Exp. Med.* 175: 1135 (1992); D. J. Peacock et al., *Arthritis Rheum.* 35: S51 (1992) (abstract); D. J. Peacock et al., *Arthritis Rheum.* 35: S140 (1992) (abstract)). A potent inhibitor of angiogenesis, AGM-1470 is a synthetic derivative of fumagillin, a naturally occurring product of *Aspergillus fumigatus fresenius* (D. Ingber et al., *Nature* 348: 555 (1990). AGM-1470 has demonstrated in vivo efficacy against solid tumors in animal models (D. Ingber et al. (1990), supra; H. Brem & J. Folkman, *J. Ped. Surg.* 28: 445 (1993) and in vitro benefits in human tumor studies (Y. Takamiya et al., *J. Neurosurg.* 78: 470 (1993). It is currently undergoing phase I trials in patients with Kaposi's Sarcoma and AIDS. In adjuvant and CIA rat models of synovitis, AGM-1470 has been shown to effectively prevent pannus formation if given prior to arthritis onset and to partially regress established arthritis (D. J. Peacock et al., *J. Exp. Med.* 175: 1135 (1992); D. J. Peacock et al., *Arthritis Rheum.* 35: S51 (1992) (abstract)).

The properties of Taxol were discussed above, with respect to its antineoplastic and antirheumatic action.

Standard anti-rheumatic therapy has typically involved the trial of sequential single therapeutic drugs in an effort to control progressive disease. Recent interest has focused on combination therapy where two or more agents are used to potentially increase overall efficacy and to reduce the incidence of adverse effects. Beneficial results with traditional disease modifying anti-rheumatic drugs (DMARDs) in combination have been difficult to demonstrate in humans (H. E. Paulus, *Sem. Arthritis Rheum.* 23 (Suppl. 1): 19 (1993)). AGM-1470 and Taxol, which represent two new classes of agents with specific mechanisms of action, were chosen as ideal candidates for concurrent use in an effort to increase their already considerable individual effectiveness in the CIA animal system.

Materials and Methods

Experimental Design

Syngeneic 8 week old female Louvain (LOU) rats were used in all experimental protocols. Under ether anesthesia, rats were immunized intradermally on day 0 with 0.5 mg of native chick CII (Genzyme, Boston, Mass.) solubilized in 0.1M acetic acid and emulsified in IFA (Difco, Detroit, Mich.) (D. E. Trentham et al. (1977), supra). Synovitis typically develops in the hind legs of 90–100% of rats within 10–12 days. 100% of rats by definition had arthritis entering the study. Four protocols (total n=61) consisted of a control group given no active agent (n=12), or AGM-1470 (n=14) and Taxol (n=11) administered as single agents, or in combination (n=24). AGM-1470 was solubilized in normal saline, with 10% ethanol and 5% gum arabic, and administered on alternate days by subcutaneous injection of 0.3 ml containing a dose of 27.5 mg/kg. Taxol (Sigma, St. Louis, Mo.) was solubilized in a 1: 1 ethanol/cremophor EL (Sigma, St. Louis, Mo.) solution. Normal saline was added to make a final concentration of 2.4 mg/ml Taxol in 5% ethanol and 5% cremophor prior to j.p. injection. The dosing schedule of single agent Taxol was on alternate days and consisted of 0.5 ml/rat (10 mg/kg Taxol) for the first 3 doses, followed by a 25% reduced maintenance dosage of 7.5 mg/kg thereafter. All treatment protocols began on the day of arthritis onset and continued for the duration of the 29 day study. An initial pilot study of rats given combination AGM-1470 and Taxol therapy demonstrated rapid and near total suppression of arthritis, but with a high mortality within 11 days of its initiation. This indicated that a reduction in the Taxol dose, when used concurrently with AGM-1470, was necessary. The resulting combination protocol with AGM-1470 employed Taxol at 7.5 mg/kg for all doses.

Arthritis Assessment

The degree of arthritis severity was recorded by daily scoring of each paw. An integer scale of 0–4 was used to quantify the level of erythema and swelling with 0=normal and 4=maximum. The sum of all four paws (a maximum score of 16 per rat) represented the arthritis index (D. E. Trentham (1977), supra). Because CIA typically affects only the hind legs, a score of 6 to 8 reflects severe arthritis. Photographs of selected limbs were obtained on day 29.

Radiologic scoring of hind limbs was determined by an investigator, blinded to treatment protocol, on day 29 using a scoring system of 0–3, based on the degree of soft tissue swelling, joint space narrowing, periosteal new bone formation, and the presence of erosions and/or ankylosis (0=normal, 3=maximum joint destruction) (E. Brahn & D. E.

Trentham, *Clin. Immunol. Immunopathol.* 31: 124 (1984)). The radiographic joint index represented the sum of both hind legs, with a maximum possible score of 6.

Cellular and Humoral Immunity

An in vivo radiometric ear assay completed on day 28 was used to measure DTH to CII (D. E. Trentham & C. E. Brinckerhoff, *J. Immunol.* 129: 2668 (1982)). A radiometric ear index $\geq 1.4$ is considered a significant response to CII, based on previous studies. IgG antibodies to CII were measured in quadruplicate aliquots from serum obtained on day 19 post arthritis onset using an enzyme-linked immunosorbent assay (ELISA) (E. Brahn & D. E. Trentham, *Cell. Immunol.* 86: 421 (1984); E. Brahn & D. E. Trentham, *Cell. Immunol.* 118: 491 (1989)). Antibody titers were expressed as the absorbance at 490 nm of a 1: 2560 dilution of serum and normalized against a previously standardized curve.

Statistical Analysis

Student's t-test was used to analyze group means of continuous variables. Results were considered significant at $p<0.05$.

Results

Figure 5:
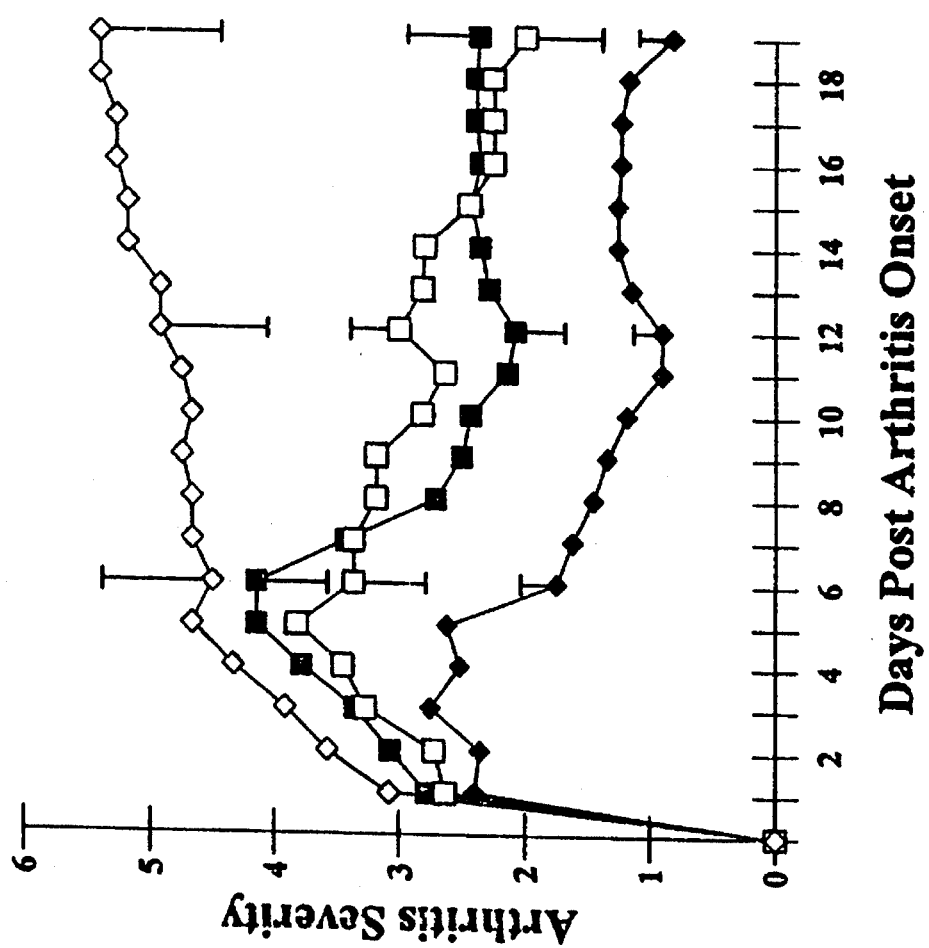
FIG. 5 is a graph showing arthritis severity in rats (Example 2) with established arthritis treated With AGM-1470 (■), Taxol (□), AGM-1470 in combination with Taxol (♦), and controls (◇)

A significant reduction in arthritis severity ($p<0.05$) was evident in rats treated with single agent AGM-1470 or Taxol, compared to controls rats, within 9 and 11 days of arthritis onset, respectively (FIG. 5; AGM-1470 (■), Taxol (□), AGM-1470 in combination with Taxol (◆), and controls (◇)) Compared to controls, rats treated with single agent AGM-1470 or Taxol had a significant reduction in clinical arthritis by Days 9 and 11 postarthritis onset, respectively ($P<0.05$). Combination therapy resulted in significant arthritis suppression, compared to control animals, by Day 4 ($P<0.05$) that continued throughout the study to Day 19 ($P<0.00001$).

The efficacy of single agent AGM-1470 or Taxol was comparable at all time points during the treatment period. There were no treatment related deaths or episodes of diarrhea in the single agent studies. Although there were no treatment related deaths in the rats receiving combination therapy with the reduced Taxol dose of 7.5 mg/kg, some rats, however, developed transient weight loss and diarrhea, and both agents were temporarily suspended between days 6 and 13 in the combination group protocol. The affected rats demonstrated reversible granulocytopenia. Within 4 days of combination therapy initiation, a significant reduction of arthritis severity compared to controls ($p<0.05$) was noted and maintained throughout the remainder of the study period ($p<0.00001$ by day 19 post arthritis onset) (FIG. 5). Combination therapy was significantly better than single agent AGM-1470 or Taxol by day 5 and 6 post onset of arthritis, respectively. The maximum mean arthritis score of rats in the combination protocol (Table 3) was 2.8 and occurred on day 3 post arthritis onset. Maximum mean arthritis scores of 4.2 and 3.8 were attained by Taxol and AGM-1470 treated rats, respectively, on day 5 post arthritis onset, compared to control rats whose arthritis continued to increase throughout the study to a maximum score of 5.4 on day 19 post arthritis onset (FIG. 5). Selected hind limbs of control and combination protocol rats at the termination of the 29 day study are depicted in FIGS. 6A–6D. Marked clinical inflammation and bone destruction were found in the control group and this was absent in the combination therapy group. Blinded radiographic scores of the hind limbs of combination and AGM-1470 treated rats were significantly lower than controls (Table 3). Radiographic scores of combination therapy rats were significantly lower than the single agent Taxol treated rats.

Figure 6A:
FIG. 6A is a photograph of a hind limb from a control group rat 19 days after arthritis onset (Example 2), showing swelling and other changes characteristic of arthritis.
Figure 6C:
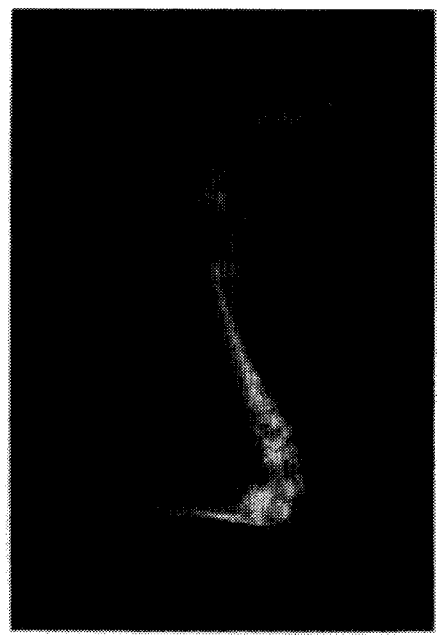
FIG. 6C is a photograph of a hind limb from a combination therapy group rat (Example 2), showing regression of previously occurring swelling and other changes characteristic of arthritis.
Figure 6B:
FIG. 6B is a radiograph of the hind limb shown in FIG. 6A, showing soft tissue inflammation and bone destruction.
Figure 6D:
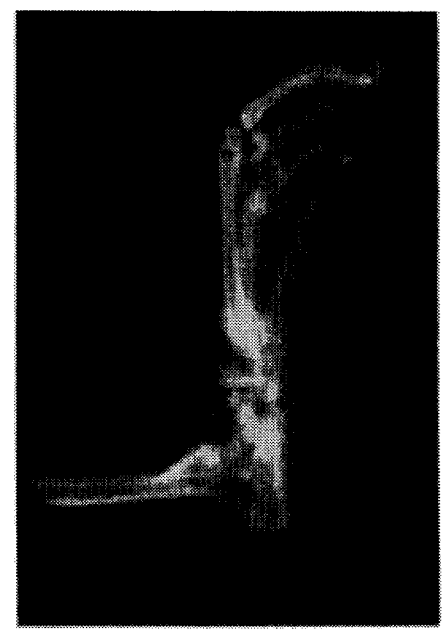
FIG. 6D is a corresponding radiograph of the hind limb shown in FIG. 6C, showing regression of soft tissue inflammation and bone destruction.

Clinical and radiographic findings on Day 19 postarthritis onset are shown in FIGS. 6A–6D. FIGS. 6A and 6B show a representative hind limb and corresponding radiograph from a control group rat. Note the marked soft tissue inflammation and joint destruction. FIGS. 6C and 6D show a representative hind limb and corresponding radiograph from a combination therapy group rat. This limb had an earlier maximum clinical arthritis severity score of 3 on Day 3 postarthritis onset. With continued therapy, it regressed to a clinical and blinded radiographic score of 0 (i.e., no evidence of arthritis).

TABLE 3

Arthritic and Immunologic Assessments in CIA (Example 2)

| Group | Arthritis index[a] | Maximum arthritis score | Radiographic index[b] | Antibody to CII[c] | DTH to CII[d] |
|---|---|---|---|---|---|
| Control | 5.40 ± 0.98 | 5.40 ± 0.98 | 4.30 ± 0.72 | 0.14 ± 0.009 | 2.84 ± 0.40 |
| AGM-1470 | 2.36 ± 0.59[e] | 4.14 ± 0.52 | 1.58 ± 0.34[f] | 0.12 ± 0.011 | 4.24 ± 0.45 |
| Taxol | 2.00 ± 0.63[e] | 3.81 ± 0.60 | 2.27 ± 0.71 | 0.11 ± 0.005[g] | 3.49 ± 0.66 |
| Combination | 0.82 ± 0.27[h] | 2.76 ± 0.33[f,i] | 0.94 ± 0.29[j] | 0.11 ± 0.008[e] | 3.28 ± 0.32 |

[a]Mean arthritis index on Day 19 postarthritis onset ± SEM.
[b]Mean radiographic index on Day 19 postarthritis onset.
[c]Mean OD at 490 nm of a 1:2560 dilution.
[d]Mean radiometric ear index.
[e]$P < 0.05$ compared to controls.
[f]$P < 0.005$ compared to controls.
[g]$P < 0.01$ compared to controls.
[h]$P < 0.00001$ compared to controls; $P < 0.05$ compared to single agent Taxol and AGM-1470.
[i]$P < 0.05$ compared to AGM-1470.
[j]$P < 0.0001$ compared to control group; $P < 0.05$ compared to Taxol group.

Sensitization to CII, as measured by DTH and IgG anti-CII antibodies, was evident in all treated and control groups by day 19 after arthritis onset. However, the mean anti-CII antibody titer was significantly higher in the control groups compared with the Taxol ($p<0.01$) and combination therapy ($p<0.05$) groups. DTH levels were comparable within all treatment groups and control rats.

In the study reported in this Example, the concurrent administration of AGM-1470 and Taxol resulted in significant reduction of arthritis severity as judged by both clinical and radiographic criteria. Suppression of established arthritis was studied because either agent alone, if given early prior to clinical arthritis, will prevent CIA. Prevention of CIA has always been easier to achieve than regressing existing disease and may not be a clinically relevant comparison for progressive human synovitis conditions such as rheumatoid arthritis. The therapeutic benefit of AGM-1470 and Taxol in combination was better clinically and radiographically compared to either agent alone. The magnitude of differences in radiographic scores was less than the clinical scores. This may reflect the nonquantitative aspect of the radiographic scoring system for the degree of soft tissue swelling, resulting in less sensitivity at milder disease levels. Previous work has demonstrated that AGM-1470 functions as an angiogenesis inhibitor in CIA and adjuvant arthritis models and not as an immunosuppressive agent (D. J. Peacock et al., *J. Exp. Med.* 175: 1135 (1992); D. J. Peacock et al., *Arthritis Rheum.* 35: S51 (1992) (abstract))).

Conditions manifesting pannus require neovascularization to occur and to be maintained. AGM-1470 is one of the few angiogenesis inhibitors to be evaluated in vivo. It has demonstrated efficacy in angiogenesis inhibition and suppression of solid tumor growth in a variety of cancer models (D. Ingber et al. (1990), supra; H. Brem & J. Folkman (1993), supra; Y. Takamiya et al. (1993), supra). It has little effect on nonreplicating endothelial cells and angio-independent ascitic leukemic cells, suggesting that it is not merely an antiproliferative agent (D. Ingber et al. (1990), supra). Suppression of vasculitis in a murine model of Kawasaki's Disease has also been demonstrated using AGM-1470 (D. J. Peacock et al., *Arthritis Rheum.* 36: S93 (1993) (abstract)). The primary mechanisms of action of AGM-1470 are currently under investigation. In vitro, AGM-1470 inhibits fibroblast growth factor (FGF) induced stimulation of endothelial cell migration, proliferation, and capillary tube formation (D. Ingber et al. (1990), supra; H. Brem et al., *Surg. Forum* 42: 439 (1991); M. Kusaka et al. *Biochem. Biophys. Res. Comm.* 174: 1070 (1991)), all key steps in the process of neovascularization (D. C. Billington, *Drug Des. Dis.* 8: 3 (1991)). AGM-1470 also inhibits in vivo neovascularization induced by basic FGF in the cornea micropocket model (E. M. Gonzalez et al., *Invest. Ophthamol. Vis. Sci.* 33: 777 (1992) (abstract)). Possible additional mechanisms of angioinhibition may include stimulation or inhibition of other cytokines associated with angiogenesis regulation such as TNF-α, ECGF, IFN-α and IFN-γ (J. Folkman & M. Klagsbrun (1987), supra; N. Sato et al., *J. Invest. Dermatol.* 95 (Suppl. 6): 85S (1990)). Vascular effects may also occur through various endogenous inhibitors such as TIMP-1 and TIMP-2, which regulate the activity of matrix metalloproteinases required for penetration of the basement membrane by activated endothelial cells during neovascularization (M. A. Moses et al., *Science* 248: 1408 (1990); M. A. Moses & R. Langer *J. Cell Biochem.* 47: 230 (1991)). Modest angiogenesis inhibitory activity has been associated with several agents used in autoimmune therapies. Methotrexate, cyclophosphamide, and azathioprine have a direct inhibitory effect on many cell types undergoing rapid turnover although of these, only methotrexate has been shown to be angiostatic in vitro and in vivo (S. Hirata et al., *Arthritis Rheum.* 32: 1065 (1989)). D-penicillamine, another anti-rheumatic drug, has also demonstrated an angioinhibitory capacity (T. Matsubara et al., *J. Clin. Invest.* 83: 158 (1989)). In addition, the thiol moiety of gold compounds has inhibitory effects upon macrophage mediated angiogenic activity (A. E. Koch et al., *Agents Actions* 34: 350 (1991)). Finally, chloroquine and the sulfasalazine metabolite, sulfapyridine, have both been ascribed angiogenesis inhibitory properties (A. L. Inyang et al., *Cell Biol. Int. Rep.* 14: 35 (1990); R. Madhok et al., *J. Rheum.* 18: 199 (1991)). Despite these findings, other physiologic actions characteristic of these anti-rheumatic agents make it difficult to determine the importance of anglogenesis inhibition in their activity in autoimmune therapy.

Taxol, with its unique action on the microtubule system, has both immunologic and anti-inflammatory effects on autoimmune mechanisms (E. K. Rowinsky et al. (1990), supra). In vitro studies have suggested that Taxol acts as a phase-specific anti-cancer agent that is particularly cytotoxic for cells undergoing mitosis (N. M. Lopes et al., *Cancer Chemother. Pharmacol.* 32: 235 (1993)). A potent inhibitor of eukaryotic cell replication, Taxol blocks cells in the late G2 mitotic phase (S. B. Horwitz (1992), supra). Human leukemic cells exposed to Taxol in vitro display bundles of disorganized microtubules and abnormal spindle aster formations (P. Schiff & S. B. Horwitz, *Proc. Natl. Acad. Sci.* (USA) 77: 1561 (1980)).

The mechanism of arthritis suppression with Taxol may be multifold. Rapidly proliferating inflammatory pannus cells may be more susceptible to Taxol's phase specific cytotoxic effects. By interfering with normal microtubule function, Taxol inhibits cell mitosis, migration, chemotaxis, intracellular transport, and neutrophil $H_2O_2$ production (E. K. Rowinsky et al. (1990), supra). Suppression of intracellular transport by Taxol may also interfere with macrophage processing and presentation of CII, since it can permanently block the induction of CIA if given early (see Example 1). Because microtubules are critical components of coordinated endothelial cell migration (D. S. Ettenson & A. I. Gotlieb, *Lab. Invest.* 66: 722 (1992); S. R. Gordon & C. Staley, *Cell Motil. Cytoskel.* 16: 47 (1990)), one of the key steps in neovascularization, Taxol could have anti-angiogenic activity. Strong immune responses to CII, as measured by DTH and antibody assays, suggest that immunosuppression was not a major factor in determining therapeutic outcome in this antigen-specific, T-cell-mediated autoimmune animal model. Although antibodies to CII were statistically lower in the Taxol treated rats, the significance of this is unclear since all rats produced high titer anti-CII IgG antibodies (Table 3).

Taxol's effect on an antigen-specific humoral immune response has not been previously reported. It has been linked to inhibition of several cell mediated processes including lymphocyte proliferation (J. A. Cuthbert & J. Shay, *J. Cell Physiol.* 116: 127 (1983) and selective neutrophil/macrophage functions (R. L. Roberts et al., *J. Immunol.* 129: 2134 (1982)). By a mechanism previously described with lipopolysaccharide (LPS), Taxol upregulates TNF-α expression but down-regulates TNF-α receptors on murine macrophages (C. Bogdan & A. Ding, *J. Leukoc. Biol.,* 52: 119 (1992); C. L. Manthey et al. (1992), supra). This might be important in chronicsynovitis because prior work has demonstrated that TNF-α plays a prominent role in CIA pannus proliferation (E. Brahn et al., *Lymphokine Cytokine Res.,* 11: 253 (1992)).

Adverse effects of Taxol appeared to be enhanced by the concurrent use of AGM-1470, necessitating a reduction of Taxol dosing. However, as discussed above, therapeutic. benefits may be maintained at lower dosage levels of Taxol. Although few if any toxicities have been associated with long-term administration of AGM-1470 (H. Brem & J. Folkman (1993), supra), Taxol exposure can lead to multiple side effects, including neutropenia, major hypersensitivity reactions, cardiac arrhythmias, and neurotoxicity (E. K. Rowinsky et al., *Sem. Oncol.* 20 (Suppl. 3): 1 (1993)). Taxol treatment can also cause mitotic arrest and cell necrosis in the gastrointestinal tract (R. H. Hruban et al., *Cancer* 63: 1944 (1989)). An AGM-1470 interaction may have enhanced Taxol's i.p. cytotoxic effect on cells undergoing mitosis, resulting in the appearance of diarrhea and weight loss in the combination protocol rats. These adverse effects were reversible over several days by withholding treatment, probably aided by the rapid systemic clearance of Taxol. Future dose scheduling changes could include a more aggressive reduction of Taxol after the initial doses used in combination with AGM-1470. This might achieve and maintain maximal early suppression of CIA with minimal morbidity. Altering the sequence of drug administration may also have an effect on the overall efficacy and toxicity of AGM-1470 and Taxol co-administration. In a phase I study of Taxol and cisplatin, more profound neutropenia and decreased Taxol clearance rates were noted when Taxol administration followed cisplatin than with the alternate sequence. (E. K. Rowinsky et al., *J. Clin. Oncol.* 9: 1692 (1991)). In a separate in vitro study, optimum cytotoxic activity against L1210 leukemic cells was demonstrated when Taxol preceded cisplatin than with the alternate sequence or simultaneous drug administration (E. K. Rowinsky et al., *J. Cancer Res. Clin. Oncol.* 119: 727 (1993)).

The inflammatory processes in human autoimmune diseases such as RA are complex and involve both cellular and humeral immunity, inflammatory mediators, and multiple cytokines (E. D. Harris, Jr., *N. Eng. J. Med.* 322: 1277 (1990)). The combination of two or more agents with different targeted sites of action can provide more effective control of inflammation. This is the first reported use of AGM-1470 and Taxol in combination therapy. Significantly earlier and more effective suppression of CIA inflammation was seen compared to either single agent alone. This may be clinically important since early and aggressive control of inflammation in RA patients may improve long term outcome as defined by disability level and degree of irreversible joint damage (S. E. Gabriel & H. S. Luthra, *Mayo Clin. Proc.* 63: 58 (1988); Y. S. Sherrer et al., *Arthritis Rheum.* 29: 494 (1986)) Further study of agents with distinct and/or specific mechanisms of action in combination may lead to better treatment options.

The results reported in this Example provides a novel scheme for combined drug therapy for rheumatoid arthritis, and provides the basis for further improvement in therapy.

ADVANTAGES OF THE INVENTION

The use of Taxol in the suppression of autoimmune rheumatoid disorders provides another, significant, treatment for rheumatoid arthritis and other autoimmune forms of arthritis. The use of Taxol can suppress or ameliorate symptoms such as inflammation, swelling, abnormal neovascularization, bone erosion, or cartilage erosion. Most significantly, Taxol can be combined with other treatment methods, such as the use of angiogenesis inhibitors. Taxol works rapidly to cause regression or stabilization of symptoms, and is generally well tolerated. The results reported suggest that the use of Taxol may be adaptable to prophylaxis in susceptible individuals.

Although the present invention has been described in considerable detail with regard to certain preferred versions thereof, other versions are possible. Therefore, the spirit and scope of the appended claims should not be limited to the descriptions of the preferred versions contained herein.

I claim:

1. A method for suppression of a progressive, inflammatory, autoimmune arthritis in a mammal comprising administering to a mammal having or susceptible to arthritis Taxol in a pharmacologically acceptable carrier capable of solubilizing Taxol in a dose sufficient to suppress at least one symptom of arthritis selected from the group of inflammation, swelling, abnormal neovascularization, bone erosion, and cartilage erosion.

2. The method of claim 1 wherein the mammal is a rat and the arthritis is collagen-induced arthritis.

3. The method of claim 1 wherein the mammal is a human being and the arthritis is rheumatoid arthritis.

4. The method of claim 1 wherein the pharmacologically acceptable carrier is a 1:1 dilution of ethanol and cremophor EL, further diluted with saline.

5. The method of claim 1 wherein the dose sufficient to suppress at least one symptom of arthritis is from about 7.5 mg/kg body weight to about 10 mg/kg body weight of Taxol.

6. The method of claim 1 wherein the dose sufficient to suppress at least one symptom of arthritis is from about 0.075 mg/kg body weight to about 0.1 mg/kg body weight of Taxol.

7. The method of claim 1 wherein the dose sufficient to suppress at least one symptom of arthritis is from about 0.75 mg/kg body weight to about 1.0 mg/kg body weight of Taxol.

8. The method of claim 1 further comprising administering to the mammal an antiarthritic drug other than Taxol selected from the group consisting of a nonsteroidal antiinflammatory agent, an organic gold derivative, D-penicillamine, a 4-aminoquinoline, azathioprine, methotrexate, cyclosporin, an angiogenesis inhibitor, a monoclonal antibody to T cells, a monoclonal antibody to an adhesion molecule, and a monoclonal antibody to a cytokine or growth factor.

9. The method of claim 8 wherein the antiarthritic drug other than Taxol is the angiogenesis inhibitor O-(chloroacetylcarbamoyl) fumagillol.

10. A method for suppression of a progressive, inflammatory, autoimmune arthritis in a mammal comprising:
(a) administering to a mammal having or susceptible to arthritis Taxol in a pharmacologically acceptable carrier capable of solubilizing Taxol in a dose sufficient to suppress at least one symptom of arthritis selected from the group of inflammation, swelling, abnormal neovascularization, bone erosion, and cartilage erosion; and
(b) administering to the mammal the angiogenesis inhibitor O-(chloroacetylcarbamoyl) fumagillol in a dose sufficient to suppress at least one symptom of arthritis; the administration of both Taxol and ,AGM-1470 producing a greater degree of suppression of at least one symptom of arthritis than does the administration of the equivalent dose of either Taxol or O-(chloroacetylcarbamoyl) fumagillol alone.

11. A method for suppression of a progressive, inflammatory, autoimmune arthritis in a mammal comprising administering to a mammal having or susceptible to arthritis a Taxol derivative in a pharmacologically acceptable carrier capable of solubilizing the Taxol derivative in a dose sufficient to suppress at least one symptom of arthritis selected from the group of inflammation, swelling, abnormal neovascularization, bone erosion, and cartilage erosion.

12. The method of claim 11 wherein the mammal is a rat and the arthritis is collagen-induced arthritis.

13. The method of claim 11 wherein the mammal is a human being and the arthritis is rheumatoid arthritis.

14. The method of claim 11 further comprising administering to the mammal an antiarthritic drug other than the Taxol derivative selected from the group consisting of a nonsteroidal antiinflammatory agent, an organic gold derivative, D-penicillamine, a 4-aminoquinoline, azathioprine, methotrexate, cyclosporin, an angiogenesis inhibitor, a monoclonal antibody to T cells, a monoclonal antibody to an adhesion molecule, and a monoclonal antibody to a cytokine or growth factor.

15. The method of claim 14 wherein the antiarthritic drug other than the Taxol derivative is the angiogenesis inhibitor O-(chloroacetylcarbamoyl) fumagillol.

* * * * *

UNITED STATES PATENT AND TRADEMARK OFFICE
CERTIFICATE OF CORRECTION

PATENT NO. : 5,583,153

DATED : December 10, 1996

INVENTOR(S) : Brahn

It is certified that error appears in the above-identified patent and that said Letters Patent is hereby corrected as shown below:

```
Column 16, line 42, "chronicsynovitis" should read --chronic
synovitis--
```

Signed and Sealed this

Twenty-fourth Day of June, 1997

Attest:

BRUCE LEHMAN

Attesting Officer     Commissioner of Patents and Trademarks